United States Patent
Corbin et al.

(10) Patent No.: US 6,232,502 B1
(45) Date of Patent: May 15, 2001

(54) METHOD OF MAKING METHYLAMINES USING CHABAZITE CATALYSTS

(75) Inventors: David Richard Corbin, West Chester, PA (US); Raul Francisco Lobo, Newark; Stephan Schwarz, Wilmington, both of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/462,454

(22) PCT Filed: Jun. 30, 1998

(86) PCT No.: PCT/US98/13502

§ 371 Date: Mar. 24, 2000

§ 102(e) Date: Mar. 24, 2000

(87) PCT Pub. No.: WO99/02483

PCT Pub. Date: Jan. 21, 1999

Related U.S. Application Data

(60) Provisional application No. 60/051,905, filed on Jul. 8, 1997, and provisional application No. 60/064,493, filed on Nov. 5, 1997.

(51) Int. Cl.$^7$ .................................................. C07C 209/16
(52) U.S. Cl. ............................ 564/474; 564/479; 564/480
(58) Field of Search .................................. 564/474, 479, 564/480

(56) References Cited

U.S. PATENT DOCUMENTS 4,544,538  10/1985  Zones .................................. 423/326

FOREIGN PATENT DOCUMENTS

| | | | |
|---|---|---|---|
| 0 183 423 A1 | 6/1986 | (EP) | C07C/85/06 |
| 0 210 718 A1 | 2/1987 | (EP) | C07C/87/08 |
| 0 632 012 A1 | 1/1995 | (EP) | C07C/209/16 |
| 0 744 395 A1 | 11/1996 | (EP) | C07C/211/04 |
| WO 95/18675 | 7/1995 | (WO) | B01J/29/06 |

Primary Examiner—Johann Richter
Assistant Examiner—Brian J. Davis

(57) ABSTRACT

A method for making monomethylamine, dimethylamine and trimethylamine, in which methanol and/or dimethylether and ammonia are contacted in the presence of an acidic zeolite chabazite catalyst is disclosed. The method suppresses the production of trimethylamine and optimizes dimethylamine and monomethylamine yields.

8 Claims, No Drawings

METHOD OF MAKING METHYLAMINES USING CHABAZITE CATALYSTS

This application is a 371 of PCT/US78/13502 filed Jun. 30, 1998 which claims priority benefit of U.S. Provisional Application No. 60/051,905 filed Jul. 8, 1997 and U.S. Provisional Application No. 60/064,493 Nov. 5, 1997.

FIELD OF THE INVENTION

This invention generally relates to a process for the manufacture of monomethylamine, dimethylamine and trimethylamine in which methanol and/or dimethylether and ammonia are contacted in the presence of an acidic zeolite chabazite catalyst. In particular, the reactants are contacted in the presence of an acidic zeolite chabazite catalyst, wherein the ratio of silicon to aluminum (Si:Al) in said catalyst is at least about 5:1.

BACKGROUND OF THE INVENTION

Methylamines are generally prepared commercially by continuous reaction of methanol and ammonia in the presence of a dehydration catalyst such as silica-alumina. The reactants are typically combined in the vapor phase, at temperatures in the range of 300° C. to 500° C., and at elevated pressures. Trimethylamine is the principal component of the resulting product stream accompanied by lesser amounts of monomethylamine and dimethylamine. The methylamines are used in processes for pesticides, solvents and water treatment. From a commercial perspective, the most valued product of the reaction is dimethylamine in view of its widespread industrial use as a chemical intermediate (e.g., for the production of dimethylformamide). Thus, a major objective of those seeking to enhance the commercial efficiency of this process has been to improve overall yields of dimethylamine and monomethylamine, relative to trimethylamine. Among the approaches taken to meet this goal are recycling of trimethylamine, adjustment of the ratio of methanol to ammonia reactants and use of selected dehydrating or aminating catalyst species. Many patents and technical contributions are available because of the commercial importance of the process. A summary of some of the relevant art for methylamine synthesis using zeolite catalysts is disclosed in U.S. Pat. No. 5,344,989 (Corbin et al.).

Zeolites chabazite, where the zeolite is derived from mineral sources and the silicon to aluminum ratios in said zeolites is less than about 2:1, as well as zeolites rho are known to be useful as catalysts for methylamines. See U.S. Pat. No. 5,569,785 (Kourtakis et al.) and references cited therein. The use of natural, H-exchanged and M-exchanged chabazites, where M is one or more alkali metal cations selected from the group consisting of Na, K, Rb and Cs is disclosed in U.S. Pat. No. 4,737,592 (Abrams et al.).

U.S. Pat. No. 5,399,769 (Wilhelm et al.) discloses an improved methylamines process using synthetic chabazites as catalysts. Runs 3–5 in Table 5 show the methylamines distribution for different synthetic chabazites with a Si:Al ratio of about 2.5:1. The molar ratio of ammonia to methanol was 3.5: 1; such an excess of ammonia is known to decrease trimethylamine formation. The percentage of dimethylamine shown for each run was 26, 48.7 and 51.5, respectively.

What are needed and are of significant interest to the chemical industry are process improvements which suppress production of trimethylamine and optimize dimethylamine and monomethylamine yields. Other objects and advantages of the present invention will become apparent to those skilled in the art upon reference to the detailed description which follows hereinafter.

SUMMARY OF THE INVENTION

The invention provides a method for the production of dimethylamine (i.e., $(CH_3)_2NH$ or DMA), monomethylamine (i.e., $CH_3NH_2$ or MMA) and trimethylamine (i.e., $(CH_3)_3N$ or TMA), comprising contacting methanol and/or dimethylether and ammonia in amounts sufficient to provide a carbon/nitrogen (C/N) ratio from about 0.2 to about 1.5, at a reaction temperature from about 250° C. to about 450° C., in the presence of a catalytic amount of an acidic zeolite which has a chabazite crystalline structure, and wherein the ratio of silicon to aluminum (Si:Al) in said zeolite is at least about 5:1.

DETAILED DESCRIPTION OF THE PREFERRED EMBODIMENTS

For a general description of zeolites, see U.S. Pat. No. 4,737,592 (Abrams et al.), which description is incorporated herein by reference. Chabazite, a mineral zeolite, has a structure consisting of identical, near-spherical "chabazite cages," each composed of two 6-rings at top and bottom, six 8-rings in rhombohedral positions, and six pairs of adjacent 4-rings. Each cage is interconnected to six adjacent units by near-planar, chair-shaped 8-rings. Mineral and synthetic chabazites prepared from inorganic materials can be characterized by the formula:

$M_a{}^nAl_{12}Si_{24}O_{72}.40H_2O$

In this formula, the product of a and n is 12, and M generally refers to a cation preferably selected from Ca, Mg, Na and K. The cations can be exchanged for $H^+$ using mineral acids, by ion exchange or by conversion to an ammoniated form which can then be converted to the acid form by calcination at elevated temperatures, generally ranging from about 400 to about 600° C.

Acidic zeolites which have the chabazite crystal structure, and wherein the ratio of silicon to aluminum in said zeolites is at least about 5:1 can be prepared by heating an aqueous mixture containing an organic nitrogen-containing compound, a silicon oxide source and an aluminum oxide source to a temperature of at least 100° C. The heating is continued until crystals of the desired chabazite structure zeolite are formed and then recovering the crystals. Preferably, the organic nitrogen-containing cations are derived from 1-adamantine, 3-quinuclidinol and 2-exo-aminonorbornane.

The preparation of acidic zeolites having the chabazite crystal structure is described in U.S. Pat. No. 4,544,538 (Zones), which is incorporated hereby in its entirety by reference.

If desired, the silica alumina ratio of both natural and synthetic chabazites can be increased by procedures known in the art such as leaching with chelating agents, e.g., EDTA, or dilute acids.

The process of the present invention comprises reacting methanol and/or dimethylether (DME) and ammonia, in amounts sufficient to provide a carbon/nitrogen (C/N) ratio from about 0.2 to about 1.5, in the presence of a catalytic amount of an acidic zeolite chabazite, wherein the acidic zeolite chabazite has a ratio of silicon to aluminum of at least about 5:1, at a temperature from about 250° C. to about 450° C. Reaction pressures can be varied from about 1–1000 psig (7–7000 kPa) with a methanol/DME space time of 0.01 to 80 hours. The resulting conversion of methanol and/or DME to methylamines is generally in excess of 85% (on a carbon basis) and selectivity (on a carbon basis) to dimethylamine is generally greater than 60%. In addition, selectivity to and yield of trimethylamine is suppressed. Thus, carbon yields of dimethylamine generally exceed 60% and carbon yields of trimethylamine are generally less than 10% under the process conditions of the present invention.

The molar equilibrium conversion of methanol and ammonia to a mixture of the Methylamines at 400° C. and a C/N ratio of 1.0 is 17:21:62 (MMA:DMA:TMA).

The process variables to be monitored in practicing the process of the present invention include C/N ratio, temperature, pressure, and methanol/DME space time. The latter variable is calculated as the mass of catalyst divided by the mass flow rate of methanol and DME introduced to a process reactor (mass catalyst/mass methanol+DME fed per hour.)

Generally, if process temperatures are too low, low conversion of reactants to dimethylamine and monomethylamine will result. Increases in process temperatures will ordinarily increase catalytic activity, however, if temperatures are excessively high, equilibrium conversions and catalyst deactivation can occur. Preferably, reaction temperatures are maintained between 270° C. and 370° C. more preferably 290° C. to 350° C. with lower temperatures within the ranges essentially preferred in order to minimize catalyst deactivation. At relatively low pressures, products must be refrigerated to condense them for further purification adding cost to the overall process. However, excessively high pressures require costly thick-walled reaction vessels. Preferably, pressures are maintained at 10–500 psig (70–3000 kPa). Short methanol/DME space times result in low conversions and tend to favor the production of monomethylamine. Long methanol space times may result either in inefficient use of catalyst or production of an equilibrium distribution of the products at very high methanol/DME conversions. Generally, methanol/DME space times of 0.01–80 hours are satisfactory, with methanol/DME space times of 0.10–1.5 hours being preferred (corresponding to methanol/DME space velocities of 0.013–100 g methanol+DME/g of catalyst/hour, preferably 0.67–10 g of methanol+DME/g of catalyst/hour).

The molar reactant ratio of methanol and/or dimethylether to ammonia, herein expressed as the C/N ratio (g atoms C/g atoms N), is critical to the process of the present invention. As the C/N ratio is decreased, production of monomethylamine is increased. As the C/N ratio is increased, production of trimethylamine increases. Catalyst deactivation is also greater at high C/N ratios. Accordingly, for best results, C/N ratios should be maintained between 0.2 and 1.5, and preferably from 0.5 to 1.2 in conducting the process of the present invention.

The efficiency of the process of the invention is measured by overall conversion of methanol and/or DME to methylamines, and by selectivity of dimethylamine production. For example, if methanol (MeOH) is used as the sole reactant, overall conversion is determined by comparison of the amount (in moles) of methanol in the product mixture, which is considered to be unconverted, to the amount in the reactant feed. Thus, overall conversion in carbon percent is given by:

$$100(1-(X_{MeOH})/(X_{MeOH}+X_{MMA}+2X_{DMA}+3X_{TMA}+2X_{DME})).$$

Selectivity of methanol to monomethylamine (MMA) in carbon percent, is given by:

$$100(X_{MMA})/(X_{MMA}+2X_{DMA}+3X_{TMA}).$$

Similarly, selectivity of methanol to trimethylamine (TMA), in carbon percent, is given by:

$$100(3X_{TMA})/(X_{MMA}+2X_{DMA}+3X_{TMA}).$$

Selectivity to dimethylamine (DMA) is calculated by analysis of product composition. Thus, selectivity to DMA, in carbon percent, is provided by the following expression:

$$100(2X_{DMA})/(X_{MMA}+2X_{DMA}+3X_{TMA}).$$

Finally, selectivity to dimethylether (DME) in mole percent is given by:

$$100(X_{DME})/(X_{MMA}+X_{DMA}+X_{TMA}+X_{DME});$$

where X in the above equations is the number of moles of the listed compounds.

For efficient operation, the catalyst must be selective at high conversions (87–98%) and a C/N ratio of 0.5–1.2.

In practicing the process of this invention, the zeolite catalyst can be combined with another material resistant to the temperature and other conditions employed in the process. Such matrix materials include synthetic or natural substances such as clays, silicas and metal oxides.

Comparison of selectivities for different samples should be made at similar conversions since selectivity varies with conversion. At low conversions, MMA production is favored, at very high conversions, the reaction will approach an equilibrium distribution and thus result in increased TMA production.

Selectivities can be further improved by modifying the catalyst with a coating, an example of which is described in Bergna et al., U.S. Pat. Nos. 4,683,334 and 4,752,596, the entire contents of which are incorporated by reference herein. Specifically, to improve selectivity, coating of an acidic zeolite which has a chabazite crystalline structure, wherein the ratio of silicon to aluminum (Si:Al) in said zeolite is at least about 5:1 can be accomplished in the following manner: (1) a sample of the catalyst is exposed to the ambient atmosphere and is immersed in tetraethylorthosilicate (TEOS) for 2 hours; (2) the sample is filtered and dried at room temperature overnight; (3) the sample is then heated in flowing nitrogen at 550° C. for 3 hours. The preceding treatment can be performed with one or more compounds containing at least one element selected from silicon, aluminum, boron and phosphorus, to deposit substantially on the external surfaces of the acidic zeolite with the chabazite crystalline structure at least 0.05 weight % of the element.

Without further elaboration, it is believed that one skilled in the art can, using the preceding description, utilize the present invention to its fullest extent. The following specific embodiments are, therefore, to be construed as merely illustrative, and are not to limit the remainder of the invention in any way whatsoever.

EXAMPLE 1

Preparation of Synthetic Chabazite (S-CHA) and

Its Use in the Preparation of Methylamines

Zeolite S-CHA (Si:Al=12.0:1) was prepared in a similar manner to the method of Zones, U.S. Pat. No. 4,544,538, the contents of which are incorporated herein by reference, using N,N,N-trimethyl-1-adamantammonium iodide as the organic template (i.e., structure directing agent). The zeolite was calcined at 550° C. to remove the organic template, ion-exchanged with ammonium nitrate to form NH$_4$—S—CHA, and finally calcined at 450° C. in air for 8 hours to obtain the catalytically active acidic H-S-CHA.

Before use in the reactor, the zeolite was pressed into pellets and crushed and sieved to 20 to 40 mesh (0.84 to 0.42 mm). One gram of the resulting catalyst was placed in a stainless steel U-tube reactor, 0.25 in (0.64 mm) in diameter and 18 to 20 inches length (45.7 to 50.8 cm). First, the reactor was heated to reaction temperature in a fluidized sand bath. The reaction pressure was maintained at 200 psig (1480 kPa) to resemble commercial production conditions. Reactants methanol and ammonia were fed to a pre-heater which consisted of an 80 in (2.03 m) length by ⅛ in (0.32 mm) diameter stainless steel coil at a molar ratio of about 1, vaporized and then passed through the reactor into contact with the catalyst sample. The reactor effluent was continuously measured by gas chromatography for ammonia, dimethylether (DME), methanol, water, and mono-, di- and trimethylamine. The percentage selectivities of conversion to each methylamine species are given in Table 1, below, reported at 90% methanol conversion for both runs.

Comparative Example A

Commercial H-Chabazite

A commercially available sample of H-chabazite (Si:Al= 2.6:1) obtained from PQ Corporation, Valley Forge, Pa., was used as the methylamines catalyst. The apparatus and procedure were the same as that of Example 1. The percentage selectivities of conversion to each methylamine species are also given in Table 1, below, reported at 90% methanol conversion.

Comparative Example B

MAPO-34

A catalyst consisting of the aluminophosphate molecular sieve MAPO-34, which has a chabazite crystalline structure and consists of MgO, Al$_2$O$_3$ and P$_2$O$_5$ (2 wt % Mg, 13.8 wt % Al and 18.9 wt % P), was prepared according to the procedure disclosed in U.S. Pat. No. 4,567,029 (Wilson et al.), the entire contents of which are incorporated by reference herein, and was used as the methylamines catalyst. Such catalysts can also be obtained from UOP Chemical Catalysts, Des Plaines, Ill, under the designation MAPO-34 which is the Mg form of the MeAPO-34 series of aluminophosphate molecular sieves. The apparatus and procedure were the same as that of Example 1. The percentage selectivities of conversion to each methylamine species are also given in Table 1, below, reported at 28% methanol conversion.

TABLE 1

| Ex. | Reaction Temp | Contact Time[a] | MMA % | DMA % | Combined MMA + DMA | TMA % | DME % |
|---|---|---|---|---|---|---|---|
| 1 | 350 | 25 | 23 | 73 | 96 | 5 | <0.5 |
|   | 350[b] | 20 | 29 | 66 | 95 | 5 | <0.5 |
| A | 300 | 28 | 17 | 53 | 70 | 30 | <0.5 |
| B | 350 | 64 | 47 | 25 | 72 | 28 | 10 |

[a]Contact time is in minutes
[b]A different sample of Zeolite S-CHA was tested

What is claimed is:

1. A method for the production of monomethylamine, dimethylamine, and trimethylamine comprising contacting methanol and/or dimethylether and ammonia in amounts sufficient to provide a carbon/nitrogen (C/N) ratio from about 0.2 to about 1.5 and at a reaction pressure from 7–7000 kPa and a reaction temperature from 250° C. to 450° C., in the presence of a catalytic amount of an acidic zeolite which has a chabazite crystalline structure, wherein said chabazite is characterized by a ratio of silicon to aluminum (Si:Al) of at least 12:1 and wherein methanol and/or dimethylether is selectively converted to monomethylamine, dimethylamine and trimethylamine.

2. The method of claim 1 wherein the reaction pressure is from 70–3000 kPa.

3. The method of claim 1 wherein a methanol and/or dimethylether space time of 0.01 to 80 hours is utilized.

4. The method of claim 1 wherein the conversion of methanol and/or dimethylether to monomethylamine, dimethylamine, and trimethylamine is greater than 85% on a carbon basis.

5. The method of claim 1 wherein the selectivity of conversion, on a carbon basis, to dimethylamine is greater than 60%.

6. The method of claim 1 wherein the selectivity of conversion, on a carbon basis, to trimethylamine is less than 10%.

7. The method of claim 1 wherein the reaction temperature is from 270° C. to about 370° C. and the reaction pressure is from 70–3000 kPa.

8. The method of claim 1 wherein said acidic zeolite has been modified by treatment with one or more compounds containing at least one element selected from silicon, aluminum, boron and phosphorus, to deposit thereon at least 0.05 weight percent of the element.

* * * * *